(12) United States Patent
Williams et al.

(10) Patent No.: US 8,227,190 B2
(45) Date of Patent: Jul. 24, 2012

(54) APPROACH TO MOLECULAR DIAGNOSIS OF HUMAN PAPILLOMAVIRUS-RELATED DISEASES

(75) Inventors: Inna R. Williams, Rockville, MD (US); Attila T. Lorincz, North Potomac, MD (US); Aisling O'Hara, Frederick, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 241 days.

(21) Appl. No.: 11/753,454

(22) Filed: May 24, 2007

(65) Prior Publication Data

US 2007/0243552 A1    Oct. 18, 2007

Related U.S. Application Data

(63) Continuation of application No. 10/411,830, filed on Apr. 11, 2003, now Pat. No. 7,361,460.

(51) Int. Cl.
| | |
|---|---|
| C07H 21/04 | (2006.01) |
| C07K 16/00 | (2006.01) |
| C12Q 1/68 | (2006.01) |
| C12Q 1/70 | (2006.01) |
| G01N 33/53 | (2006.01) |

(52) U.S. Cl. ........... 435/6.11; 435/5; 435/7.1; 536/24.3; 530/387.1

(58) Field of Classification Search .................. None
See application file for complete search history.

(56) References Cited

U.S. PATENT DOCUMENTS

| | | | |
|---|---|---|---|
| 5,807,692 | A | 9/1998 | Kinzler et al. |
| 5,889,169 | A | 3/1999 | Beach et al. |
| 5,919,624 | A * | 7/1999 | Ried et al. ................ 435/6 |
| 5,919,634 | A * | 7/1999 | Eyre ....................... 435/7.1 |
| 6,027,905 | A | 2/2000 | Keesee et al. |
| 6,043,030 | A | 3/2000 | Beach et al. |
| 6,211,334 | B1 | 4/2001 | Beach et al. |
| 2002/0082392 | A1 | 6/2002 | Beach et al. |
| 2002/0106685 | A1 | 8/2002 | Henning et al. |

FOREIGN PATENT DOCUMENTS

| | | |
|---|---|---|
| EP | 0 294 659 A | 12/1988 |
| WO | WO 99/21014 | 4/1999 |
| WO | WO 99/29890 A | 6/1999 |
| WO | WO 01/11361 A2 | 2/2001 |
| WO | WO 02/08764 A1 | 1/2002 |

OTHER PUBLICATIONS

Hildesheim, A. et al., J. Infect. Dis., vol. 169, pp. 235-240 (1994).*
Klaes, R. et al., Int. J. Cancer, vol. 92, pp. 276-284 (2001).*
Demeter, L. M. et al., Hum. Pathol., vol. 25, pp. 345-348 (1994).*
Raju, G.C. et al., Int. J. gynecol. Pathol., vol. 13, pp. 337-341 (1994).*
Zeng, Z. et al., Appl. Immunohistochem. Mol. Morph., vol. 10, pp. 15-19 (2002).*
Cameron, R.I. et al., Histopathology, vol. 41, pp. 313-321 (2002).*
Broker et al., "A Molecular Portrait of Human Papillomavirus Carcinogenesis", Cancer Cells, vol. 7, pp. 197-208, 1989 (Roche EU Opposition).
Higgins et al., "Transcription Patterns of Human Papillomavirus Type 16 in Genital Intraepithelial Neoplasia: Evidence for Promoter Usage within the E7 Open Reading Frame during Epithelial Differentiation", Journal of General Virology, vol. 73, pp. 2047-2057, 1992 (Roche EU Opposition).
Karlsen et al., "Use of Multiple PCR Primer Sets for Optimal Detection of Human Papillomavirus", Journal of Clinical Microbiology, pp. 2095-2100, Sep. 1996 (Roche EU Opposition).
Park et al., "Physical Status and Expression of HPV Genes in Cervical Cancers", Gynecologic Oncology, vol. 65, pp. 121-129, 1997 (Roche EU Opposition).
Stoler et al., "Human Papillomavirus Type 16 and 18 Gene Expression in Cervical Neoplasias", Human Pathology, vol. 23, No. 2, pp. 117-128, Feb. 1992 (Roche EU Opposition).
De Villiers et al., "Classification of Papillomaviruses", Virology, vol. 324, pp. 17-27, 2004.
Howley et al., "A Rapid Method for Detecting and Mapping Homology between Heterologous DNAs", Journal of Biological Chemistry, vol. 254, No. 11, pp. 4879-4883, Jun. 10, 1979.
Law et al., "Conserved Polynucleotide Sequences Among the Genomics of Papillomaviruses", Journal of Virology, vol. 32, No. 1, pp. 199-207, Oct. 1979.
Heilman et al., "Cloning of Human Papilloma Virus Genomic DNAs and Analysis of Homologous Polynucleotide Sequences", Journal of Virology, vol. 36, No. 2, pp. 395-407, Nov. 1980.
Howard et al., "Optimizing the Hybrid Capture II Human Papillomavirus Test to Detect Cervical Intraepithelial Neoplasia", Obstetrics and Gynecology, vol. 100, No. 5, Part 1, pp. 972-980, Nov. 2002.
Mazzuli et al. J. Clinical Microbiol. vol. 37, No. 4, pp. 958-963, (Apr. 1999).
B.D. Hames, et al., "Nucleic Acid Hybridization. A Practical Approach." 1985.
Greg T. Hermanson, et al., "Immobilized Affinity Ligand Techniques." 1992.
Richard F. Taylor, "Protein Immobilization. Fundamentals and Applications." 1991.
American Cancer Society, Cancer Facts and Figures, 2000, Atlanta, Georgia.
Bosch et al. "The Causal Relation Between Human Papillomavirus and Cervical Cancer". J Clin Pathol Apr. 2002; 55:244-65.
Brooks et al. "E7 proteins from oncogenic human papillomavirus types transactivate p73: role in cervical intraepithelial neoplasia". Br J Cancer Jan. 21, 2002; 86(2):263-8.

(Continued)

Primary Examiner — Teresa E Strzelecka
(74) Attorney, Agent, or Firm — Milbank, Tweed, Hadley & McCloy, LLC

(57) ABSTRACT

The present invention relates to an accurate, sensitive, and efficient sequential or concurrently sequential method for molecular diagnosis of human papillomavirus (HPV)-based disease, where the method improves the accuracy and reliability of diagnostic and prognostic assessments of HPV-based disease. The method of the invention comprises a primary screen of a sample for HPV nucleic acids, followed by a secondary screen for molecular markers, such as proliferation and cell cycle control group protein markers. The sequential or concurrently sequential method significantly reduces the number of false positive results.

6 Claims, No Drawings

OTHER PUBLICATIONS

Brown et al. "Cost-effectiveness of 3 methods to enhance the sensitivity of Papanicolaou testing". *JAMA* Jan. 27, 1999; 281(4):347-53.

Doeberitz, *Pap Report* 13: 65-74, 2002.

Feichter et al. "Task force consensus report on HPV-related changes of the lower female genital tract". *Acta Cytol.* Jul.-Aug. 2002; 46(4):630-2.

Jeon et al. "Integration of human papillomavirus type 16 into the human genome correlates with a selective growth advantage of cells". *J Virol.* May 1995; 69(5):2989-97.

Ponten et al. "Strategies for global control of cervical cancer". *Int J Cancer.* Jan. 3, 1995; 60(1):1-26.

Russell L., *Educated Guesses: Making Policy About Medical Screening Tests.* Berkeley, University of California Press, 6-24, 1994.

Sawaya et al., "New technologies in cervical cytology screening: a word of caution". *Obstet Gynecol.* Aug. 1999; 94(2):307-10.

Schechter. "Cost-effectiveness of rescreening conventionally prepared cervical smears by PAPNET testing". *Acta Cytol.* Nov.-Dec. 1996; 40(6):1272-82.

Sherman et al. "Performance of a semiautomated Papanicolaou smear screening system: results of a population-based study conducted in Guanacaste, Costa Rica". *Cancer.* Oct. 25, 1998;84(5):273-80.

Walboomers et al. "Human papillomavirus is a necessary cause of invasive cervical cancer worldwide". *J Pathol. Journal of Pathology*, Sep. 1999; 189:12-19.

M. Howard, MSc., J. Sellors, MD, MSc. and J. Kaczorowski, Ph.D, "Optimizing the Hybrid Capture II Human Papillomavirus Test to Detect Cervical Intraepithelial Neoplasia", vol. 100, No. 5, Part 1, Nov. 2002, pp. 972-980, PII S0029-7844(02)02315-3, The *American College of Obstetricians and Gynecologists, Published by Elsevier Science, Inc.*

A. Lorincz, PhD., "Molecular Methods for the Detection of Human Papillomavirus Infection", vol. 23, No. 3, Sep. 1996, pp. 707-730, 0889-8545/96, *Obstetrics and Gynecology Clinics of North America.*

Agoff, S., et al., "p16$^{INK4a}$ Expression Correlates with Degree of Cervical Neoplasia: A Comparison with Ki-67 Expression and Detection of High-Risk HPV Types," *Mod. Pathol.*, 2003 16(7):665-73.

Almendral, J., et al. "Cloning and sequence of the human nuclear protein cyclin: Homology with DNA-binding proteins," *Proc. Nat'l Acad. Sci. USA*, 1987 84(6):1575-9.

Bibbo, M., et al., "Procedure for Immunocytochemical Detection of p16$^{INK4A}$ Antigen in Thin-Layer, Liquid-Based Specimens," *Acta. Cytol.*, 2002 46(1):25-9.

Bonds, M., et al., "Immunohistochemical Localization of Cdc6 in Squamous and Glandular Neoplasia of the Uterine Cervix," 2002 126(10):1163-8.

Bravo, R., et al., "Identification of a nuclear and of a cytoplasmic polypeptide whose relative proportions are sensitive to changes in the rate of cell proliferation," *Exp. Cell Res.* 1981 136(2):311-9.

Cheung, T. et al. "Aberrant expression of p21$^{WAF1/CIP1}$ and p27$^{KIP1}$ in cervical carcinoma," *Cancer Lett.* 2001 172(1):93-8.

Duncan, E., et al., "Genetic Changes Associated with Immortalization. A Review," *Biochemistry (Mosc)* 1997 62(11):1263-74.

Freeman, A., et al., "Minichromosome Maintenance Proteins as Biological Markers of Dysplasia and Malignancy," *Clin. Cancer Res.* 1999 5(8):2121-32.

Geradts, J., et al., "Immmunohistrochemical Detection of the Alternate *INK4α*-encoded Tumor Suppressor Protein p14$^{ARF}$ in Archival Human Cancers and Cell Lines Using Commercial Antibodies: Correlation with p16$^{INK4a}$ Expression," *Mod. Pathol.* 2001 14(11):1162-8.

Keating, J., et al., "Ki-67, Cyclin E, and p16$^{INK4}$ Are Complimentary Surrogate Biomarkers for Human Papilloma Virus-Related Cervical Neoplasia," *Am. J. Surg. Pathol.* 2001 25(7):884-91.

Keating, J., et al., "Surrogate Biomarkers of HPV Infection in Cervical Neoplasia Screening and Diagnosis," *Adv. Anat. Pathol.* 2001 8(2):83-92.

Keesee, S., et al., "Fully Automated Proteomic Detection of Cervical Cysplasia,"*Analyt. Quant. Cytol. Histol.* 2002 24(3):137-46.

Lie, A., et al., "Expression of p53, MDM2, and p21 Proteins in High-Grade Cervical Intraepithelial Neoplasia and Relationship to Human Papillomavirus Infection," *Int. J. Gynecol. Pathol.* 1999 18(1):5-11.

Lin, W., et al., "Molecular Papanicolaou tests in the twenty-first century: Molecular analyses with fluid-based Papanicolaou technology," *Am. J. Obstet. Gynecol.* 2000 183(1):39-45.

Maeda, M., et al., "Relevance of the rates of PCNA, Ki-67 and p53 expression according to the epithelial compartment in cervical lesions," *Pathologica* 2001 93(3):189-95.

Mandelblatt, J., et al., "Benefits and Costs of Using HPV Testing to Screen for Cervical Cancer," *JAMA* 2002 287(18):2372-81.

McCluggage, W., et al., "Immunohistochemical Detection of Metallothionein and MIB1 in Uterine Cervical Squamous Lesions," *Int. J. Gynecol.. Pathol.* 1998 17(1):29-35.

Mittal, K., et al., "Proliferating Cell Nuclear Antigen (Cyclin) Expression in Normal and Abnormal Cervical Squamous Epithelia," *Am. J. Surg. Pathol.* 1993 17(2):117-122.

Miyachi, K., et al., "Autoantibody to a nuclear antigen in proliferating cells," *J. Immunol.* 1978 121(6):2228-34.

Murphy, N., et al., "p16$^{INK4A}$ as a marker for cervical dyskaryosis: CIN and cGIN in cervical biopsies and ThinPrep™ smears" *J. Clin. Pathol.* 2003 56(1) 56-63.

Negri, G., et al., "p16$^{INK4a}$ Is a Useful Marker for the Diagnosis of Adenocarcinoma of the Cervix Uteri and Its Precursors: An Immunohistochemical Study With Immunocytochemical Correlations" *Am. J. Surg. Pathol.* 2003 27(2):187-93.

Niculescu, A., et al., "Effects of p21$^{Cip1/Waf1}$ at Both the $G_1$/S and the $G_2$/M Cell Cycle Transitions: pRb Is a Critical Determinant in Blocking DNA Replication and in Preventing Endoreduplication," Mol. Cell Biol. 1998 18(1):629-43.

Ogata, K., et al., "Monoclonal Antibodies to a Nuclear Protein (PCNA/Cyclin) Associated with DNA Replication," *Exp. Cell Res.* 1987 168(2):475-86.

Patterson, B., et al., "Molecular biomarker-based screening for early detection of cervical cancer," *Acta. Cytol.* 2001 45(1):36-47.

Pientong,C., et al., "Immunocytochemical Detection of p16$^{INK4a}$ Protein in Scraped Cervical Cells," *Acta. Cytol.*, 2003 47(4):616-23.

Robbins, B. et al., "Immunohistochemical Detection of Proliferating Cell Nuclear Antigen in Solid Human Malignancies," *Arch. pathol. Lab. Med.* 1987 111(9):841-5.

Sahebali, S., et al., "Ki-67 immunocytochemistry in liquid based cervical cytology: useful as an adjunctive tool?", *J. Clin. Pathol.* 2003 56(9):681-6.

Sano, T., et al., "Overexpression of p16 and p14ARF is associated with human papillomavirus infection in cervical squamous cell carcinoma and dysplasia," *Pathol. Int.* 2002 52(5-6):375-83.

Saqi, A., et al., "Overexpression of p16$^{INK4A}$ in Liquid-based Specimens (SurePath )™ as Marker of Cervical Dysplasia and Neoplasia," *Diagn. Cytopathol.* 2002 27(6):365-70.

Sherman, M., et al., "Effects of Age and Human Papilloma Viral Load on Colposcopy Triage: Data from the Randomized Atypical Squamous Cells of Undetermined Significance/Low-Grade Squamous Intraepithelial Lesion Triage Study (ALTS)", *J. Nat'l Cancer Inst.* 2002 94(2):102-7.

Skomedal, H., et al. "Aberrant Expression of the Cell Cycle Associated Proteins TP53, MDM2, p21, p27, cdk4, Cyclin D1, RB, and EGFR in Cervical Carcinomas", *Gynecol. Oncol.* 1999 73(2):223-8.

Tjalma, W.A., et al. "The importance of biological factors (bcl-2, bax, p53, PCNA, MI, HPV and angiogenesis) in invasive cervical cancer" *Eur. J. Obstet. Gynecol.* 2001 97(2):223-30.

Vassilakos, P., et al. "Primary screening for cervical cancer precursors by the combined use of liquid-based cytology, computer-assisted cytology and HPV DNA testing" *Br. J. Cancer* 2002 86(3):382-8.

Weaver, E.J., et al. "Cyclin E Expression and Early Cervical Neoplasia in ThinPrep Specimens" *Acta. Cytol.* 2000 44(3):301-4.

Williams, G.H., et al. "Improved cervical smear assessment using antibodies against proteins that regulate DNA replication" *Proc. Nat'l Acad. Sci. USA* 1998 95(25):14932-7.

Baldwin, Peter et al., "Translational approaches to improving cervical screening," *Nature Reviews Cancer*, 2003 vol. 3, pp. 217-223.

Flores, Yvonne, et al., "Design and method of the evaluation of an HPV-based cervical cancer screening strategy in Mexico: The Morelos HPV Study," *salud pública de mexico*, 2002, 44(4):2002-7.

Flores, Yvonne, et al., "Improving cervical cancer screening in Mexico: Results from the Morelos HPV Study," *salud pública de mexico*, 2003, 45(3):S388-98.

Herbsleb, Marlene, et al., "Telomerase activity, MIB-1, PCNA, HPV 16 and p53 as diagnostic markers for cervical intraepithelial neoplasia," *APMIS*, 2001, vol. 109, pp. 607-617.

Lörincz, Attila, et al., "Molecular Methods for the Detection of Human Papillomavirus Infection," *Obstetrics and Gynecology Clinics of North America*, 1996 23(3):707-30.

Lörincz, Attila, et al., "Screening for cervical cancer: New alternatives and research," *salud pública de mexico*, 2003, 45(3):S376-87.

PCT International Search Report dated Feb. 22, 2005.

* cited by examiner

APPROACH TO MOLECULAR DIAGNOSIS OF HUMAN PAPILLOMAVIRUS-RELATED DISEASES

This application is a continuation of application Ser. No. 10/411,830, filed on Apr. 11, 2003, now U.S. Pat. No. 7,361,460, the disclosure of which is herein incorporated by reference in its entirety.

FIELD OF THE INVENTION

The present invention is generally related to the field of molecular assays and specifically to the area of assays for the assessment of disease using a sensitive, accurate assay for diagnosis and prognosis of human papillomavirus (HPV)-related diseases.

BACKGROUND OF THE INVENTION

The detection and diagnosis of disease is of obvious importance for the treatment of disease. Numerous characteristics of diseases have been identified and many are used for the diagnosis and prognosis of disease. Many diseases are preceded by, and are characterized by, changes in the state of the affected cells. Changes may include the expression of viral genes in infected cells, changes in the expression patterns of genes in affected cells, changes in enzymatic activities, and changes in cell morphology. The detection, diagnosis, and monitoring of diseases may be aided by the assessment of such cell states, especially by improving the accuracy of detection.

The worldwide annual incidence of cervical cancer is approximately 500,000 cases[1,2]. The current diagnostic assay for early cervical cancer detection is the Papanicolaou (Pap) test which is a simple morphological screening method of examining strained exfoliative cells. It is used most commonly to detect cancers of the cervix, but it may be used for tissue specimens from any organ. The findings are usually reported descriptively and grouped into several classifications, including the Papanicolaou and the cervical intraepithelial neoplasia (CIN) classifications.

The Pap test contributed to a 74% decline in deaths due to cervical cancer in the United States between 1955 and 1992[3]. However, the sensitivity of the Pap test for high-grade cervical lesions (cervical intraepithelial neoplasia grade 3 or CIN 3) is not very high, typically ranging from as low as 50% for conventional Pap tests to 85% for the newer liquid cytology tests[4]. Routine use of advanced cytology-based automated reading technologies such as Auto-Pap® 300 QC. AUTO-Cyt®, and Cyto-Savant™ is not a favorable approach due to high cost[5] and only minor increases in sensitivity for CIN 3[6]. The clinical data suggest that HPV DNA tests are more sensitive (about 90 to 95%) than either the conventional (50 to 70%) or liquid-based (60 to 85%) Pap tests. Combination of the Pap test with the HPV DNA test reduces false-negative cases and produces combined sensitivity for CIN 3 at 95% to 100%. However, false negative cytology tests account for at least 25% of invasive cancer cases in the United States[7]. Additionally, false-positive cases are another important limitation of the cytology approach.

Alternative diagnostic approaches are to couple the Pap test with a test for either HPV DNA[8,9,10] or cellular molecular markers[11,12,13]. The combination of the Pap test with a HPV DNA test achieves high sensitivity and can partially address the relatively high rate of HPV positive cases in women without prevalent cervical neoplastic disease. There is an increasing acceptance for those who apply appropriate algorithms in recommending women who are positive for HPV alone to make follow up appointments with longer intervals compared to those women who are positive for both the HPV nucleic acid test and the Pap test who are recommended to have immediate attention. The use of these algorithms and recommendations will be of clinical benefit. High-risk HPV DNA is highly associated with cervical cancer[14], however, most HPV infections do not lead to cervical cancer. It is estimated that 5% to 10% of normal women are HPV infected by carcinogenic HPV types, and of these up to one-quarter may be expected to develop high grade cervical lesions[15]. Women over 30 years of age are more likely to develop neoplastic disease than younger women[16].

Two formal classification systems are utilized for identification of cervical cancer precursor conditions. The CIN system relates to the tissue biopsies classification and comprises of Negative; mild cervical dysplasia or CIN 1; moderate dysplasia or CIN 2; severe dysplasia (including carcinoma in situ) or CIN 3; and carcinoma. The Bethesda Classification system relates to Pap changes and comprises of within normal limits (WNL) and benign cellular changes (equivalent to Negative); atypical squamous cell of undetermined significance (ASCUS) or atypical glandular cell of undetermined significance (AGCUS) favor benign (no equivalent in the CIN system); ASCUS or AGCUS favor dysplasia (no equivalent in the CIN system); low grade squamous intraepithelial lesion (LSIL) (equivalent to CIN 1); high grade squamous intraepithelial lesion (HSIL) (equivalent to CIN 2-3); and carcinoma. (PATH Outlook Vol 18, #1, 2000; Jelovsek F R Woman's Diagnostic Cyber).

Human papillomavirus (HPV) induces benign epithelial proliferations of the skin and mucosa in humans and is associated with anogenital neoplasias and carcinomas. Human papillomaviruses characterized to date are associated with lesions confined to the epithelial layers of skin, or oral, pharyngeal, respiratory, and, most importantly, anogenital mucosae. HPV is a virus that is the cause of common warts of the hands and feet, as well as lesions of the mucous membranes of the oral, anal, and genital cavities. The virus may be transmitted through sexual contact and is a precursor to cancer of the cervix. Non-limiting examples of diseases, disorders, and conditions associated with HPV include cervical intraepithelial neoplasia (CIN), and cancer, cervical dysplasia, vaginal cancer, vaginal dysplasia, vulvar cancer, penile cancer, anal cancer, oral cancer, atypical squamous cells including atypical squamous cells of undetermined significance (ASCUS) and atypical squamous cells, high-grade squamous intraepithelial lesion (HSIL), genital warts, plantar warts, butcher's warts, and flat warts, condylomata, epidermo dysplasia verruciformis and other skin diseases, laryngeal papilloma, oral papilloma and conjunctival papilloma. More than 70 types of HPV have been identified, many of which have been isolated from anogenital lesions.

HPV types may be divided into three groups according to their biological oncogenic potential, where some are associated with cancerous and pre-cancerous conditions. Low-risk HPV types are more frequently associated with low grade squamous intraepithelial lesions (LSIL; suspect CIN 1 lesions) and condyloma acuminatum. This group comprises, but is not limited to, low-risk HPV types 6, 11, 42, 43, 44, and others. Intermediate-risk HPV types comprise, but are not limited to HPV types 31, 33, 35, 39, 51, 52, 56, 58, 59, and 68. High-risk HPV types comprise, but are not limited to HPV types 16, 18, and 45. High-risk HPV types are more frequently associated with high-grade squamous intraepithelial lesions (HSIL; suspect CIN 2, CIN 3) and invasive carcinoma of uterine cervix.

The viral genome may be divided into three regions: (1) the upstream regulatory region (URR) or long control region (LCR), containing control sequences for HPV replication and gene expression; (2) the viral early gene region, encoding, among others, the E2, E6 and E7 genes; and (3) the late region, encoding the L1 and L2 genes.

HPV gene expression in high-grade premalignant disease or cancer appears restricted to the early genes, possibly due to cellular differentiation arrest induced by the viral E6 and E7 genes. In comparison to active HPV infection, E6 and E7 gene control in cancer is deranged by mutations in the viral URR and, in integrated viral fragments, by the disruption of the viral E2 gene, stabilization of E6 and E7 mRNAs, and influences at the cellular integration site. Cervical cells containing extrachromosomal HPV genomes rapidly segregate and are outgrown in culture by cells that contain integrated viral genomes[17].

Cervical neoplastic progression and cancer are highly associated with HPV persistence and viral DNA integration in the cellular genome. These primary molecular events, characteristic for high-risk HPV DNA subtypes, result in overexpression of the viral oncogenes E6 and E7. The presence of high-risk HPV E6 and E7 proteins leads to inactivation of the important tumor-suppression proteins p53 and pRB and their associated pathways[18]. As a result, p53- and pRB-associated genes and their products (mRNA and protein) are aberrantly expressed. Some aberrantly expressed gene products are called markers due to their readily detectability and association with neoplastic progressions. Thus, another alternative approach to improve sensitivity and/or specificity of the Pap test is to combine with marker-based screening. However, the combination of Pap test with molecular markers will also have to account for false negatives and false positives due to limited marker sensitivity and specificity (without information on high-risk HPV DNA) for neoplastic progression[13]. The published studies show high sensitivity of the molecular markers for high grade squamous intraepithelial lesion (HSIL) specimens. However, a high rate of certain marker-positive cases (approximately 12%-26%) for the within normal limits (WNL) group, (approximately 74%-88%) for atypical squamous cells of undetermined significance (AS-CUS) and low grade squamous intraepithelial lesion (LSIL) groups have also been demonstrated[11,20,21,23]. A high-rate of false positive cases is thus evident for some marker and Pap test combinations.

Several methods have been used to diagnose clinical or subclinical infection with HPVs including clinical observation, cytological screening by Pap test, electron microscopy, immunocytochemistry, and DNA hybridizations. However, a definitive diagnosis of HPV infection depends on the detection of nucleic acids (DNA or RNA) or proteins of the virus. The detection of HPV DNA by nucleic-acid-based assays may identify 20-30% of women with cervical disease who have false-negative results by Pap test screening. The presence of HPV DNA in the cervical lesions of older women has a higher predictive value for the progression of cervical intraepithelial neoplasia to invasive cancer than in younger women. Thus, there is a need for a more accurate, sensitive, and efficient method of screening clinical specimens for neoplastic disease than the time consuming and subjective Pap cytology test screenings. There is also a need for further improvements to HPV nucleic acid testing alone or the combination of Pap test screening and either HPV DNA or molecular marker tests.

Accordingly, it is an object of the present invention to provide an accurate, sensitive, and efficient method for molecular diagnosis and prognosis of HPV-based disease, where the method as a whole incorporates added specificity, enabling individual steps of the method to use lower stringency.

It is another object of the present invention to provide an assay to improve the accuracy and reliability of diagnostic and prognostic assessments of HPV-based disease.

It is a further object of the present invention to provide a method for assessing the risk that a patient infected with HPV will have or will develop HPV-based high grade neoplastic disease.

Yet a further object of the present invention is to provide a method for monitoring the effectiveness of treatment of HPV-based disease.

Another object of the present invention is to provide a scale identifying the degree of HPV high risk disease progression.

A further object of the present invention to provide kits for diagnosing, prognosing, and assessing the stage of HPV-based disease.

SUMMARY OF THE INVENTION

The present invention relates to a novel method for molecular diagnosis and prognosis of human papillomavirus (HPV)-related diseases, disorders, and conditions. This method relates to a sequential or concurrently sequential method comprising (1) an HPV nucleic acid test, preferably an HPV DNA or HPV RNA test; followed by (2) a test for molecular markers, preferably specific protein markers. This novel approach will enable the distinction of progressive HPV-related neoplastic disease from benign and non-progressive lesions. Additionally, this combination of tests performed sequentially or concurrently sequentially acts as a more accurate and sensitive tool for diagnosis and staging of cancer, specifically cervical cancer, by significantly reducing the number of false positive results. The number of false positive results is significantly reduced by employing both the HPV nucleic acid test and the test for specific protein markers, such as but not limited to cell proliferation and cell cycle control group proteins. The present invention may be used to assess the stage or risk of a disease as indicated by the state of the cells. It may also be used to guide or assess the effectiveness of a therapy for a disease by identifying appropriate therapy based on the indicated cell state or by indicating any change in the state of cells subjected to the therapy.

DESCRIPTION OF THE INVENTION

The present invention relates to the identification and monitoring of human papillomavirus (HPV)-infected cells. One embodiment of the present invention relates to a method of measuring the presence and levels of expression of genes involved in a disease state, and comparing their expression to each other or to reference genes, as an indication of the state of the cells. Such measurements are combined with a molecular marker assay to increase the accuracy and reliability of the assessment of the disease state by significantly reducing the number of false positive results. This sequential or concurrently sequential method comprising an HPV nucleic acid test and a molecular marker assay, such as protein marker, incorporates specificity in diagnosing and prognosing HPV infected individuals.

One advantage of the specificity being incorporated in the sequential or concurrently sequential method is that the individual steps may use lower stringency conditions. For example, the HPV nucleic acid test of the sequential or concurrently sequential method may be less stringent as compared to the results of the HPV nucleic acid test alone.

Although this step of the method is less restrictive, overall the sequential or concurrently sequential method removes cross reactivity since specificity is incorporated. This method may also be used to guide or assess the effectiveness of a therapy for a disease by identifying the appropriate therapy based on the indicated disease state or by indicating any change in the state of cells subjected to the therapy. The present invention is generally directed to a sequential or concurrently sequential method comprising measuring gene or viral genome presence or expression followed by detecting particular markers indicative of disease state. "Sequential" is defined herein as relating to or arranged in a sequence, or following in order, or in regular succession without gaps. "Concurrently sequential" is defined herein as relating to separate processes of separate samples, where the samples are the same representative group, and the processes may be performed at the same time. Whereas, "simultaneous" is defined herein as processes of the same sample set, where the processes occur, happen, or exist at the same time.

A further embodiment of the present invention implements an accurate and sensitive sequential or concurrently sequential method of detecting and assessing disease and the stage of disease progression in a biological sample from a subject by measuring HPV nucleic acid infection, HPV DNA or HPV RNA, followed by detecting specific molecular markers. In particular, this embodiment relates to a protein-based molecular detection method for detecting protein markers, such as cell proliferation and cell cycle control markers. This novel sequential or concurrently sequential method is expected to be more specific in identifying women who are more likely to have high-grade cervical disease among those who are infected by carcinogenic HPV DNA types or corresponding HPV RNA. The test may also have utility in detecting potentially progressive HPV infections in women who do not have prevalent high-grade cervical neoplastic disease. This novel molecular diagnostic method is a sequential or concurrently sequential method that utilizes HPV nucleic acid detection as the primary screening test followed by protein marker detection as a secondary screening test, where the protein markers are cell proliferation and cell cycle control group proteins.

Many diseases are characterized by specific cellular phenotypes and gene expression patterns. For example, neoplastic and cancerous cells generally exhibit certain distinctive morphologies and growth characteristics. Molecular characteristics, such as gene mutations and gene expression patterns are also a good indicator of disease progression. Virally infected cells may exhibit different morphologies and cellular gene expression patterns, including expression of viral genes. In the present invention, the characteristics of the cell state, such as changes in the presence and expression of genes, including viral genes, may be used to determine or assess the human papillomavirus disease state from a patient sample.

The characteristics to be detected are generally specific to the cell state of interest and the disease suspected of being present in the cell sample. Such characteristics may generally be divided into two types, cytological characteristics and molecular characteristics. As described herein, cytological characteristics are characteristics such as, for example, overall cell shape, nuclear shape, nuclear size, and appearance. The primary identification and classification of many neoplastic and cancerous cells have traditionally been accomplished by using cytological characteristics. Identification of cytological characteristics is generally slow and tedious, and requires a relatively high level of training, and generally cannot be easily automated. As used herein, molecular characteristics are determined by the presence and state of particular molecular species, such as proteins, nucleic acids, and metabolites. Such molecular characteristics are generally identified by detecting and measuring the particular molecules of interest.

In one embodiment of the present invention, a method for the diagnosis and prognosis of HPV infection comprises a primary screen for detecting HPV nucleic acids by hybridization with DNA or RNA probes directed against specific types of HPV, such as those relating to high risk HPV. The probes are type-specific and may be labeled or unlabeled. If the probe is labeled, the label may be isotopic or non-isotopic, preferably non-isotopic; however, the preferred probe is not labeled or modified. Although all of the hybridization methods are highly sensitive and specific, each has certain specifications associated with the time needed, the expertise, or the sample used in the procedure, but most of all their sensitivity. Several different HPV hybridization methodologies may be used including, but not limited to, Southern blot, Dot blot, Slot blot, and in situ hybridization. Other non-limiting examples of techniques for detecting HPV nucleic acids include, branched DNA assays, transcription-mediated amplification (TMA), ligase chain reaction (LCR), self-sustained sequence replication (3SR), nucleic acid sequence based amplification (NASBA), strand displacement amplification, and amplification with Qβ replicase, and polymerase chaing reaction (PCR) including both low stringency (broadly cross-reactive) and high stringency (type-specific) methods. PCR-based methods have been used successfully for the detection and typing of genital HPV genotypes in clinical specimens, such as cervical swabs or scrapes, saline cervicovaginal ravages, frozen biopsies, and formalin-fixed paraffin-embedded tissues.

Numerous assays for the detection and measurement of gene expression products are known and may be adapted for the determination of the level of expression of genes of interest in the disclosed assay. For example, many of the techniques for the detection of HPV in general or expression of HPV genes described below may also be adapted for use in the disclosed assay for the detection of expression of HPV genes E6, E7, L1, E4, and E2. However, a preferred method of detecting HPV nucleic acids in a cell sample is by the hybrid capture technique described in WO 93/10263 by Digene, incorporated herein by reference.

Yet another embodiment of the present invention relates to the level of stringency in the HPV nucleic acid test. Since the sequential or concurrently sequential method of diagnosing and prognosing individuals infected with HPV incorporates specificity, the HPV nucleic acid test may be modified to use lower stringency conditions than when the HPV nucleic acid test is used alone. As will be understood by those skilled in the art, the stringency of hybridization may be altered in order to identify or detect identical or related polynucleotide sequences. As will be further appreciated by the skilled practitioner, the melting temperature, $T_m$, can be approximated by the formulas as known in the art, depending on a number of parameters, such as the length of the hybrid or probe in number of nucleotides, or hybridization buffer ingredients and conditions (see, for example, T. Maniatis et al., *Molecular Cloning: A Laboratory Manual*, Cold Spring Harbor Laboratory, Cold Spring Harbor, N.Y., 1982 and J. Sambrook et al., *Molecular Cloning: A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994-1995, Suppls. 26, 29, 35 and 42; pp. 2.10.7-

2.10.16; G. M. Wahl and S. L. Berger (1987; *Methods Enzymol.* 152:399-407); and A. R. Kimmel, 1987; *Methods of Enzymol.* 152:507-511).

As a general guide, $T_m$ decreases approximately 1° C.-1.5° C. with every 1% decrease in sequence homology. Also, in general, the stability of a hybrid is a function of sodium ion concentration and temperature. The hybridization reaction of the HPV nucleic acid test alone is performed under conditions of high stringency. However, since the sequential or concurrently sequential method of the present invention incorporates specificity and reduces both analytical and clinical false-positive results, the primary HPV nucleic acid screen may use lower stringency conditions. Reference to hybridization stringency, e.g., high, moderate, or low stringency, typically relates to such washing conditions.

Thus, by way of non-limiting example, "high stringency" refers to conditions that permit hybridization of those nucleic acid sequences that form stable hybrids in 0.018M NaCl at about 65° C. (i.e., if a hybrid is not stable in 0.018M NaCl at about 65° C., it will not be stable under high stringency conditions). High stringency conditions can be provided, for instance, by hybridization in 50% formamide, 5×Denhardt's solution, 5×SSPE (saline sodium phosphate EDTA) (1×SSPE buffer comprises 0.15 M NaCl, 10 mM $Na_2HPO_4$, 1 mM EDTA), (or 1×SSC buffer containing 150 mM NaCl, 15 mM Na 3 citrate $2H_2O$, pH 7.0), 0.2% SDS at about 42° C., followed by washing in 1×SSPE (or saline sodium citrate, SSC) and 0.1% SDS at a temperature of at least about 42° C., preferably about 55° C., more preferably about 65° C.

"Moderate stringency" refers, by non-limiting example, to conditions that permit hybridization in 30%-40% formamide, 5×Denhardt's solution, 5×SSPE (or SSC), 0.2% SDS at 42° C. (to about 50° C.), followed by washing in 0.2×SSPE (or SSC) and 0.2% SDS at a temperature of at least about 42° C., preferably about 55° C., more preferably about 65° C.

"Low stringency" refers, by non-limiting example, to conditions that permit hybridization in 10% formamide, 5×Denhardt's solution, 6×SSPE (or SSC), 0.2% SDS at 42° C., followed by washing in 1×SSPE (or SSC) and 0.2% SDS at a temperature of about 45° C., preferably about 50° C.

For additional stringency conditions, see T. Maniatis et al., *Molecular Cloning: A Laboratory Manual*, Cold Spring Harbor Laboratory, Cold Spring Harbor, N.Y. (1982). It is to be understood that the low, moderate and high stringency hybridization/washing conditions may be varied using a variety of ingredients, buffers and temperatures well known to and practiced by the skilled artisan.

Another embodiment of the present invention is detection and measurement of the expression levels of certain HPV genes. An impressive amount of data has been accumulated over the years showing that carcinoma of the cervix is associated with infection of certain types of HPV. Though the presence of HPV DNA in a precancerous lesion is indicative of an increased relative risk for cervical dysplasia and invasive carcinoma, it is still difficult to predict the clinical behavior of precancerous cervical lesions. Tumors arise due to the accumulation of genetic alterations which may activate oncogenes and/or inactivate tumor suppressor genes and/or genes involved in DNA damage recognition and repair.

HPV E6 and E7 proteins are two oncoproteins of high-risk HPV types (e.g., HPV-16, HPV-18), which inactivate p53 and bind or inactivate pRb respectively, and thus act as promoters of HPV-associated cancers. The expression levels of E6 and E7 oncoproteins encoded by high-risk HPV types are a sensitive and accurate measure of potential risk of an HPV infection developing into a cancerous lesion. In one embodiment of the present invention, the HPV DNA or RNA test may be assayed by measuring relative amounts of E6 and/or E7 expression levels and E2 and/or L1 in an HPV-infected lesion to determine the ratio of E6 and/or E7 to L1 and/or E2, where this ratio is a direct measure of risk and susceptibility to the development of a cancerous lesion, as described in U.S. Pat. No. 6,355,424 to Digene, incorporated herein by reference.

As can be readily discerned, each major disease state is represented by a unique expression pattern of these four genes, i.e., E6, E7, L1, and E2. Conditions expressing these genes are regarded as indicative of an increased risk of potentially serious medical aliments. Other relationships involving the relative level expression of other HPV genes (such as E1, E4, E5, and L2), and other, non-HPV genes, may also be used to assess cell state. For example, L2 and E4 are frequently associated with benign viral production diseases, and E1 is similar in profile to E2 and is often deleted in malignancies. Other relationships of expression for these HPV proteins may exist for other HPV-based diseases, and the disclosed method may be used to assess the state of such other diseases using the appropriate levels and ratios for that disease.

In one aspect of the invention, the stage and prognosis of a human papillomavirus (HPV) infection or HPV-based disease is assessed. This embodiment of the present invention involves the measurement of the level of expression of one or more HPV genes discovered to be related to the stage and nature of HPV-based disease. Genes useful for this purpose include the HPV E6, E7, L1, and E2 genes, preferably full-length genes. It has been discovered that the level of expression of these genes, the ratio of expression of these genes to each other or to one or more other genes, or both, are indicative of the stage of HPV-based disease. The level of expression is relative to other HPV genes, or the level of expression relative to a non-HPV gene, referred to herein as a reference gene. Such reference genes may be any appropriate gene (not encoded by HPV), and are, for example, housekeeping genes or other constitutively expressed genes. Examples of reference genes include actin genes, cytoskeletal genes, histone genes, tubulin genes, epidermal growth factor receptor genes, the normal p53 gene, the normal pRB gene, cyclin genes, β-globin genes, and glucose-6-phosphate dehydrogenase genes. Expression of reference genes may be measured in the same cell as the level of HPV genes are measured or in neighboring cells in the same cell sample. In such a case, the reference gene is an internal control for gene expression.

For example, the level of expression of the HPV gene and the reference gene is measured in the same cell sample. Such measurements provide an internal control of the overall expression level in a cell sample and are used to calculate a corrected level of expression for the HPV gene to allow more accurate comparisons of the level of expression between different cell samples. One form of correction is referred to as normalization. Thus, the level of expression of one or more HPV genes may be measured in two or more cell samples along with the level of expression of the same reference gene in each of the cell samples. The level of expression of the HPV genes is then normalized to each other based on differences, if any, between the measured level of expression of the reference gene in each of the samples.

Using information about the levels and ratios of HPV genes in different cell states, the stage of the disease may be assessed in several ways. In some cases, the presence or absence of detectable expression is indicative of the disease state in the infected cells. For example, a lack of E2 expression (when HPV is present) is indicative of high grade cervical intraepithelial neoplasia or cancer. In other cases, a change or difference in expression of an HPV gene product may be indicative of change occurring in the infected cell state. For example, an increased level of expression of E6 and E7—relative to, for example, an earlier sample or a reference sample—may be indicative of high grade cervical intrapeithelial neoplasia or cancer. A change in the ratio of E6 and E7 expression to E2 expression is used to identify low grade cervical intrapeithelial neoplasia or a shift from normal cells to low grade cervical intrapeithelial neoplasia. Many other combinations of comparisons are also possible.

There are several ways in which measured levels of expression of HPV genes may be compared and categorized. For example, where the expression is indicative of the cell state, expression of the HPV gene is analyzed without reference to the expression level of other genes. Where the relative level of expression of an HPV gene is indicative of the cell state, the measured level of expression is compared, for example, to the level of expression of the same type of HPV gene in a different cell sample (such as an earlier cell sample from the same source or reference cells harboring HPV), to the level of expression of a different type of HPV gene in the same or a different cell sample, to the level of expression of a non-HPV reference gene in the same cell sample, or to the level of expression of a non-HPV reference gene in reference cells.

In one embodiment of the present invention, levels and ratios of expression of HPV genes may be compared to the levels of the same genes in a cell line that contains HPV (such as HeLa or CaSki). Such cell lines provide a standard against which levels of expression of HPV genes in cell samples are compared. Such comparisons are used to assess and compare the absolute levels of expression of these HPV proteins with those in a standard or comparative cell line. Other cell lines useful for this purpose are non-cancerous cell lines infected with HPV 16 (such as W12) or HPV 31 (such as CIN-612).

The types of comparison described above may also be used with other genes and other disease states. That is, the measured level of expression of a gene of interest may be compared, for example, to the level of expression of the same type of gene in a different cell sample (such as an earlier cell sample from the same source or appropriate reference cells), to the level of expression of a different type of gene in the same or a different cell sample, to the level of expression of a reference gene in the same cell sample, or to the level of expression of a reference gene in reference cells.

For hybridization detection of HPV nucleic acids, a mixture of probes specific for these sequences from different HPV types may be used. This ensures that the method will detect expression regardless of the type of HPV involved. For some purposes, it may be desirable to use probes designed for the sequence of a certain HPV type, or a mixture of probes for only some HPV types. Such probes may or may not be type-specific depending on the differences between the sequences of the HPV nucleic acids to be detected. One useful mixture for this purpose would include probes for HPV types more closely associated with a progression to cancer. The HPV types most commonly associated with cervical cancer are types 16 and 18.

The clinical significance of introducing high-risk HPV DNA testing to routine cervical diagnosis by the conventional Pap test is well recognized. However, neither of these tests provides information about persistence of high-risk HPV infection highly associated with development of high-grade neoplasia and cancer. Additional molecular testing to measure aberrant marker expression in high-risk HPV DNA-positive cases would possibly increase the accuracy and prognostic value of a diagnosis. The combination of testing for high risk HPV DNA with protein markers greatly reduces the rate of false positives and improves the specificity of HPV DNA for more likely high-grade cervical lesions.

In a preferred embodiment of the invention, high-risk HPV DNA is measured by the hybrid capture based HC2 HPV DNA test (Digene Corporation; Gaithersburg, Md.). Briefly, clinical specimens are combined with a base solution which disrupts the virus or bacteria and thereby releases target DNA. No special specimen preparation is necessary. The target or sample DNA is then hybridized with RNA probes forming RNA:DNA hybrids. Multiple RNA:DNA hybrids are captured onto a solid phase coated with universal capture antibodies specific for RNA:DNA hybrids. Captured RNA:DNA hybrids are detected with multiple labeled antibodies, where alkaline phosphatase is one example of a label. The resulting signal may be amplified to at least 3000-fold. The bound label is detected with a substrate, such as chemiluminescent dioxetane substrate. Upon reaction, the substrate produces light that is measured on a luminometer in Relative Light Units (RLUs), thereby enabling the detection, identification, and interpretation of HPV DNA in the subject sample. Although this HPV DNA hybridization method is preferred, one skilled in the art would understand that an RNA sample and DNA probes may also be used. Furthermore, multiple testing on a single platform, a microarray for example, is preferred. The present invention is applicable to any known or future test that detects HPV by nucleic acid hybridization analysis, DNA or RNA, or that employs a nucleic acid detection test, (i.e., RNA) utilizing a ratio of expression of early versus late regions of the HPV genome.

Another embodiment of the present invention is the secondary screening diagnostic test for molecular markers. The molecular markers assayed for may include additional or surrogate marker characteristics that are not a direct cause or result of the disease, but that are related to certain disease and cell states. Non-limiting examples of such markers include polymorphic markers, human leukocyte antigens (HLA) such as B7 that predispose women for cervical carcinomas, oncogenes, p53 mutations, other cancer markers, oncosupressors, cytokines, growth factor receptors, and hormones. Such markers may be present in, or absent from, cells exhibiting state- or disease-specific characteristics, and such presence or absence may be indicative of, for example, a more severe or less severe disease state. These markers are used in conjunction with the disclosed method to infer either higher or lower risk of neoplastic disease depending on the number of abnormal scores or the magnitude of change in quantitative markers.

In particular, the molecular markers of the sequential or concurrently sequential method may preferably comprise of two levels of protein markers: (a) a proliferation group, of which a preferred member is PCNA; however, MIB-1 (also known as Ki-67), cdc6, and mcm proteins, preferably mcm2 and mcm5 may be also used; and (b) a cell cycle control group, of which a preferred member is $p16^{INK4A}$; however, $p21^{WAF1}$, $p14^{ARF}$ may be also used. Expression of the protein markers may be measured utilizing primary antibodies, highly specific for the target antigen. The expression of protein markers, such as but not limited to, cell proliferation and cell cycle control group markers, may be screened for in a subject sample by, for example, immunostaining, immunocytochemistry, by an enzyme-linked immunosorbent assay (ELISA) or an analogous test such as a LUMINEX-based protein assay, or protein microarray.

Briefly, the immunostaining procedure involves the steps of preparing the subject sample, blocking, permeabilizing, adding primary antibodies raised against the proliferation group and/or the cell cycle control group proteins, adding a labeled secondary antibody which recognizes the primary, and upon substrate reaction, detecting the signal. The preferred members of each molecular marker group, PCNA and p16$^{INK4A}$, were selected for their high affinity of the corresponding primary antibodies for the target antigen. However, additional related markers may be utilized in the test to increase the sensitivity as necessary. These primary antibodies may be utilized individually (detection of a single marker) or as a pool (detection of multiple markers simultaneously).

Proliferation and cell cycle control group proteins are preferred molecular markers of disease and cell states since abrogation of tumor-suppression functions of p53 and pRB proteins by high-risk HPV oncoproteins, E6 and E7, leads to cell cycle activation at the G1/S phase followed by promotion of the host cell and viral DNA synthesis. This phenomenon results in over-expression of the proteins associating or controlling cell proliferation, DNA replication, and the cell cycle. Cell proliferation markers are gene products which are expressed in actively dividing cells, or cells which are committed to or are entering the cell cycle. These markers are generally absent from cells which are quiescent, dormant, in stationary phase or otherwise arrested either temporarily or permanently and are not participating in the cell cycle. Non-limiting examples of cell proliferation markers include: PCNA, cdc6, mcm2, mcm3, mcm4, mcm5, mcm6, mcm7, Cdc7 protein kinase, Dbf4, Cdc14 protein phosphatase, cyclin A, Cdc45, Ki67, KiS1, and mcm10.

Cell cycle control proteins may therefore be used as markers in the screening diagnostic test of the present invention. These proteins regulate and control the cell cycle progression at particular checkpoints, directing the cell towards proliferation, growth arrest or apoptosis. Non-limiting examples of cell cycle control markers include: p16$^{INK4A}$, p14$^{ARF}$, and p21$^{WAF1}$.

A preferred cell proliferation associated protein is proliferating cell nuclear antigen (PCNA). PCNA is an S-phase associated nuclear protein and a cofactor of DNA polymerase. Overall, PCNA expression is progressively correlated with a cervical lesion grade, with about 70%-92% positive cases identified in high-grade lesions and cancer[22]. Over-expression of other proteins related to cell proliferation and DNA replication, such as, but not limited to, MIB-1 (also known as Ki-67), cdc6, mcm2, and mcm5 has been described in cervical neoplasia and carcinoma 23. For example, Ki-67 is a non-histone protein expressing in all phases of the cell cycle (with exception of the G0 phase). Cdc6, mcm2, and mcm5 are members of the pre-initiation complex of DNA replication, therefore, involved in the earlier initiation stage of the process. The described group of proteins (PCNA, Ki-67, cdc6, mcm2, and mcm5) is a good indicator of the cell proliferation status, however, not necessarily associating with neoplastic transformation. Thus, this group of proteins is distinguished as the proliferation group, although the proteins are over-expressed and are not specific for cervical neoplastic grade. Cell proliferation markers may be detected at the mRNA stage, but preferably cell proliferation markers are detected as proteins or polypeptides.

The regulatory machinery of the cell cycle is composed of cyclins, cyclin-dependent kinases (CDKs) and their inhibitors (CKIs). CKIs may be separated into two groups having the following proteins: p21$^{Waf1}$, p27$^{Kip1}$ and p57$^{Kip2}$ and the other including p15$^{Ink4b}$, p16$^{Ink4a}$, p18$^{Ink4c}$ and p19$^{Ink4d}$. A preferred cell cycle control associated protein is p16$^{INK4A}$. p16$^{INK4A}$ is a cyclin-dependent kinase inhibitor. This protein inhibits cell progression through the G1-S stage of the cell cycle and interaction with cdk4/6. p16$^{INK4A}$ is over-expressed in HPV-associated lesions, with 70%-96% positive cases for high-grade lesions[21,24]. Additionally, over-expression of other proteins related to cell cycle control, such as p14$^{ARF}$ and p21$^{WAF1}$, has been found in high grade squamous intraepithelial lesion (suspect CIN 2-3) and cervical carcinoma. Both of these proteins are involved in cell cycle arrest in the G1 and G2/M phases through MDM2 (p14$^{ARF}$) or cyclins and cdk complexes (p21$^{WAF1}$)[25]. The previously described group of proteins (p16, p14, and p21) relates to cell cycle control and associates with neoplastic transformation. Thus, this group of proteins is referred to as the cell cycle control group, specifically over-expressed in HPV-associated cervical neoplasia and cancer.

In yet another embodiment of the present invention, the sequential or concurrently sequential method is advantageous in that the number of false positive results is significantly reduced. Performing the HPV nucleic acid test and performing the protein marker test for cell proliferation and/or cell cycle control group proteins individually results in false positive results. However, the combination of these tests as described herein, increases the specificity and reduces the cross reactivity associated with false positive results. For example, Table 4 shows positive cases identified by HPV DNA and preferred molecular markers. Specifically, 8% of the normal clinical specimens (WNL) were positively identified by high risk HPV DNA screening alone; 26% of the WNL specimens were positively identified by PCNA proliferation group protein marker screening alone; 11% of the WNL specimens were positively identified by p16 cell cycle control group protein marker screening alone; 27% of the WNL specimens were positively identified by PCNA and/or p16 protein marker screening; and 3% of the WNL specimens were positively identified by HPV DNA screening and PCNA and/or p16 protein marker screening. The number of positive specimens is significantly reduced when the screening tests are combined. This may be attributed to the specificity incurred by the combination of tests. The number of false positives is reduced by the range of about 15%-100%, about 20%-90%, or about 30%-70%. One advantage of this sequential or concurrently sequential method is that the individual tests may be less stringent or restrictive since the combination of tests increases the specificity.

A further embodiment of the present invention relates to a method of assessing risk associated with cellular abnormality in a subject's sample comprising obtaining sample cells from a subject, detecting higher or lower risk HPV infection; and identifying the over-expressed molecular markers, such as proliferation and/or cell cycle control group proteins. In particular, HPV nucleic acid data are combined with protein marker expression data to provide an improved and more accurate assessment of risk for concurrent or future cervical neoplasia with fewer false results. The positive or negative results of the molecular tests, such as high-risk HPV nucleic acid and protein marker expression tests, may be based on the signal to cutoff value.

In general, a clinical specimen that is tested is positive if its specimen signal intensity to cutoff value ratio is greater than or equal to 1. The cutoff value is determined experimentally for any type of assay and may be varied from assay to assay. The cutoff value is determined using detection of assay positive controls. An assay positive control is run in replicates and its mean value should be above the mean value from detection of negative control. The difference between positive control and negative control values should be statistically reliable. Statistical reliability depends on the number of replicates in the assay and the cutoff value percent (% CV) of each value.

In one embodiment of the present invention that uses the HC2 HPV DNA assay, the cutoff value is experimentally determined using an HPV positive control having a concentration of 1 pg/ml. The assay detection results are expressed as a ratio of the specimen signal intensity in relative light units (RLU) to its cutoff value. Specimens with a specimen signal/cutoff value ratio of greater than or equal to 1 is HPV positive, and indicative of HPV infection, risk of neoplasia, and the presence or expression of HPV nucleic acids. Specimens with a specimen signal/cutoff value ratio of less than 1 is HPV negative (Digene Corporation; HR HPV DNA Test).

In particular for the protein immunostaining assay, the cutoff value is experimentally determined in the $99^{th}$ percentile optical density (OD) values generated by measuring a protein marker negative control. The assay result is expressed as a ratio of the specimen signal intensity (i.e., median OD value above the cutoff value) to the cutoff value. This signal to cutoff value ratio is also referred to as the median ratio. Specimens with a specimen signal intensity to cutoff value ratio of greater than or equal to 1, preferably greater than or equal to 1.2, are protein marker positive as described in Example 2. Specimens with a specimen signal intensity to cutoff value ratio of less than 1 are protein marker negative.

In brief, there are two methods of analyzing immunostaining: visually and by densitometry as described above. According to the visual method, the blue negative and red-brown positive stained cells are manually counted. The staining intensity is graded and scored on a scale of ½+, 1+, 2+, and 3+, where 3+ is very strong. Specimens having a score of 3% at 1+ or higher are considered to be positive for PCNA+ MIB-1. Those specimens with a positive score of 1+ are considered to be positive for p16.

In yet a further embodiment of the present invention, the results of the primary and secondary screenings are assessed. More particularly, the molecular screening tests for cervical cancer described herein enable further characterization of the specimens in relation to neoplastic grade. Molecular grades may be useful for more accurate medical follow-up procedures. The sequential or concurrently sequential method of detecting HPV nucleic acids and molecular protein marker(s) is based on whether a subject sample is positive or negative for (1) the primary HPV nucleic acid screen; and/or (2) the secondary screen for protein marker for proliferation group and/or cell cycle control group proteins.

A molecular grade 0 (MG0) is considered to be a subject sample that is negative for the primary high risk HPV nucleic acid test, and will not be tested for the secondary protein markers test. A molecular grade I (MGI) is considered to be a subject sample that is positive for the primary HPV nucleic acid screen, but negative for the secondary protein marker screen. A molecular grade II (MGII) is considered to be a subject sample that is positive for both the primary HPV nucleic acid and secondary protein marker screens. The recommendation of cervical screening management using the novel sequential or concurrently sequential diagnostic screening method and molecular classification of the present invention is to repeat routine screening for high risk HPV nucleic acid test in 3-5 years from the initial testing if the subject sample is a MG0, which indicates the absence of high-risk HPV infection and cervical neoplastic lesions. For individuals having MGI, the sequential or concurrently sequential screening method should be repeated in 3-12 months from the initial screen. This grade indicates the presence of high risk HPV DNA, but not necessarily a neoplastic lesion and it is important to determine if the HPV infection is persistent as indicated by a repeat positive HPV DNA. For individuals having a MGII, immediate referral for a colposcopy and under the physician's recommendation, any subsequent biopsy and treatment. MGII indicates the presence of high-risk HPV DNA, elevated expression of protein markers, and increased risk of neoplastic lesions and/or cervical cancer.

In yet another embodiment of the present invention, automated screening devices are preferably used in conjunction with the method of identifying HPV-related molecular markers.

The contents of all patents, patent applications, published PCT applications and articles, books, references, reference manuals and abstracts cited herein are hereby incorporated by reference in their entirety to more fully describe the state of the art to which the invention pertains.

As various changes may be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

EXAMPLES

Example 1

Protocol for Immunocytochemical Staining

Slide Preparation

Teflon-printed 8-well slides (EMS; Fort Washington, Pa.) were incubated in Histogrip (Zymed Laboratories, Inc.; South San Francisco, Calif.) for 2 min at room temperature (RT). The slides were rinsed in water (three changes) and air dried at RT.

Specimen Preparation

Aliquots of liquid cervical specimens collected either in PRESERVCYT (PC), (Cytyc Corporation; Boxborough, Mass.) or Universal Collection Media (UCM: Digene Corporation; Gaithersburg, Md.) were centrifuged at 5223 rcf for 5 minutes to obtain cell pellets (approximately 100,000-200,000 cells). The supernatants were removed and the cell pellets were resuspended in 1 ml of MUCOLEXX (Shandon Inc.; Pittsburgh, Pa.). The specimens were incubated in MUCOLEXX for approximately 15-18 hours at RT. The MUCOLEXX was removed by centrifugation at 5223 rcf for 5 minutes. The specimens were further processed through a modified protocol (TriPath; Burlington, N.C.). Briefly, the cell pellets were resuspended in 750 µl of CytoRich Preservative Fluid (TriPath) and added to the top of 750 microliters of CYTORICH Density Reagent (TriPath). The gradient mixture was centrifuged at 200 rcf for 2 minutes, followed by removal of 650 microliters of the mixture from the top. The remainder of each specimen was centrifuged at 800 rcf for 10 minutes, followed by removal of supernatants. The pelleted specimens were washed once and then resuspended in PC (Cytyc Corporation). The resuspended specimens were applied to the wells of an 8-well slide (approximately 500-1,000 cells per well), and air-dried at RT for 10-30 minutes. Dried slides were fixed in 95% ethanol for at least 10 minutes prior to immunostaining.

Immunostaining Protocol

ENVISION+ SYSTEM, HRP kit (DAKO Corporation; Carpinteria, Calif.) and protocol were utilized for immunostaining. Briefly, the slide was air dried, then dipped in Tris Buffered Saline (TBS), (DAKO Corporation). Excess TBS was gently blotted and 250 microliters of 4 mM Sodium Deoxycholate (Sigma; St. Louis, Mo.) was spread evenly over the wells. The specimens were incubated with Sodium Deoxycholate for 5 minutes at RT, followed by dipping the slide in 0.25% Triton X in TBS for 30 seconds. The slide was gently blotted and incubated with Peroxidase Blocking Agent (DAKO Corporation) for 5 minutes at RT, followed by dipping and washing in TBS for 30 seconds. Excess TBS was gently blotted, and 250 microliters of primary antibody properly diluted in Antibody Diluent was applied to the wells. The following primary antibodies were utilized: monoclonal mouse anti-human Ki-67 (MIB-1, code #M 7240; DAKO Corporation); monoclonal mouse anti-human PCNA (PC10, code #MS-106-P; Lab Vision Corporation; Fremont, Calif.), monoclonal mouse anti-human p16$^{ink4a}$ (E6H4, code #OA 315; DAKO A/S, Denmark). Some specimens were tested using a different clone of p16$^{ink4a}$: DCS-50.1/H4 from Oncogene Research Products; Boston, Mass. The slide was incubated at RT for 30 min (antibody clone DCS-50.1/H4 was used at 37° C.) in a humidity chamber, followed by 3 changes of washes in TBS for 2 minutes each. Excess TBS was gently blotted and secondary anti-mouse HRP-labeled antibody was applied per slide. The slide was incubated at RT for 30 minutes in a humidity chamber, followed by 3 changes of washes in TBS for 2 minutes each. Excess TBS was gently blotted and 250 microliters of Liquid DAB+ substrate-chromogen solution (DAKO Corporation) was applied to the slide, which was then incubated for 7 minutes at RT. The slide was dipped and washed in TBS for 1 minute, followed by washing in 95% ethanol. The slide was counterstained in Hematoxylin for 35 seconds, and washed in two changes of water. Finally, the slide was stained in 37 mM Ammonium Hydroxide (EMS; Fort Washington, Pa.), followed by washing in water and air-drying the excess liquid. The dried slide was mounted with Permanent Mounting Media (DAKO Corporation) and covered with a microglass cover slip (VWR Scientific Products; Willard, Ohio). The immunostaining was evaluated under the microscope. Cells expressing protein markers were positively stained with brown color.

Example 2

Procedure for Scoring Results

Immunostaining Evaluation by Visual Score

The immunostained specimens were scored visually. Briefly, negatively (blue) and positively (red-brown) stained cells were counted. Each specimen counting score contained at least 100-200 cells. The percentage of positive cells within the negative cell population was calculated. The staining intensity was graded at ½+ (light), 1+ (mild), 2+ (moderate), and 3+ (strong). Specimens with a score of 3% at 1+ or higher were considered to be positive for PCNA+MIB-1. Specimens with a positive score of 1+ were considered to be positive for p16.

Immunostaining Evaluation by Densitometry Software

The immunostained specimens were scored utilizing Image-Pro® Plus software (OPELCO; Dulles, Va.). Briefly, the light intensity of the manually selected cells from the color (Red, Green, Blue) photographic image was measured for cervical controls and specimens. The intensity of blue color (Hematoxylin counterstain) was filtered out by the software, and the average intensity of red and green (DAB positive stain) colors was calculated. The relative optical density (OD) was extrapolated from the standard calibration curve. An OD value of the assay cutoff was established by calculating the 99$^{th}$ percentile OD for the negative control. A median value of the specimen OD above the cutoff was calculated. The median ratio was calculated by dividing the specimen's median OD value over the cutoff. Specimens with a median ratio greater than or equal to 1, preferably greater than or equal to 1.2, were positive for protein expression.

Example 3

Identification of Positive Cases by HPV DNA and Protein Marker Analyses

Results

PRESERVCYT® (Cytyc Corporation) clinical cervical specimens were utilized for assessment of high risk HPV DNA and protein markers expression. The specimen's cytological diagnosis was confirmed by trained professionals using the Pap test results. The specimens were grouped based on cytological diagnosis rendered by trained expert cytologists as follows: a) within normal limits (WNL), b) LSIL (suspect cervical intraepithelial neoplasia 1; CIN1), comprised of mild dysplasia, c) HSIL (suspect CIN 2), comprised of moderate dysplasia, and d) HSIL (suspect CIN 3+), comprised of moderate to severe and severe dysplasia, in situ and invasive carcinoma. The cytological diagnosis was used as the "gold standard" for evaluation of the novel molecular method. The immunostaining results scored visually are presented in Table 1.

TABLE 1

Positive Cases Identified by HPV DNA and Protein Markers

| Clinical Specimen | Total # of Specimens | High Risk HPV DNA, # (%) Positive | PCNA + MIB-1 Proliferation Group, # (%) Positive | p16 Cell Cycle Control Group, # (%) Positive | PCNA + MIB-1 and/or p16, # (%) Positive | PCNA + MIB-1 and/or p16 and/or High Risk HPV DNA, # (%) Positive |
|---|---|---|---|---|---|---|
| WNL | 46 | 3 (6.5%) | 12 (26.1%) | 5 (10.9%) | 14 (30.4%) | 0 (0%) |
| HSIL (suspect CIN 2) | 62 | 55 (88.7%) | 43 (69.4%) | 33 (53.2%) | 48 (77.4%) | 43 (69.4%) |
| HSIL (suspect CIN 2-3+) | 81 | 74 (91.4%) | 61 (75.3%) | 49 (60.5%) | 67 (82.7%) | 62 (76.5%) |
| HSIL (suspect CIN 3+) | 19 | 19 (100%) | 18 (94.7%) | 16 (84.2%) | 19 (100%) | 19 (100%) |

A total of 46 cervical specimens with WNL cytological diagnoses were tested for the presence of high-risk HPV DNA using the HC2 test. The presence of high-risk HPV DNA was found in 3 out of 46 specimens (6.5%). The same group of specimens (total number 46) was tested for expression of the proliferation group of protein markers (PCNA+ MIB-1) and the cell cycle control group of markers (p16$^{INK4A}$) using the immunostaining protocol. Positive expression of proliferation markers was found in 12 out of 46 specimens (26.1%). Positive expression of p16$^{INK4A}$ was found in 5 out of 46 specimens (10.9%). Overall, 14 out of 46 WNL specimens (30.4%) were found positive for a combination of either group of protein markers (proliferation or cell cycle control), while using high-risk HPV DNA detected only 6.5% HPV positive samples. None of 14 specimens, positive for either molecular marker, was positive for high-risk HPV DNA. Thus, 0 out of 46 WNL specimens (0%) were found positive for both high-risk HPV DNA and any one or more of the protein markers. The rest of the results presented in Table 1 were interpreted in a similar fashion. Briefly, 88.7% of the HSIL (suspect CIN 2) group was found positive for high-risk HPV DNA, and 69.4% of the same group was positive for a combination of high-risk HPV DNA and either proliferation or cell cycle control markers. Additionally, 91.4% of the HSIL (suspect CIN 2-3+) group was found positive for high-risk HPV DNA, and 76.5% of the same group was positive for a combination of high-risk HPV DNA and either proliferation or cell cycle control markers. Finally, 100% of the HSIL (suspect CIN 3+) group was found positive for high-risk HPV DNA, and 100% of the same group was positive for a combination of high-risk HPV DNA and either proliferation or cell cycle control markers.

A new set of PC cervical specimens (including six specimens from the WNL group that were scored visually in Table 1) was tested for high-risk HPV DNA by the HYBRID CAPTURE (HC2; Digene Corporation) test and for expression of protein markers by the immunostaining test. The specimens were grouped based on the received cytological diagnosis as followed: a) WNL, b) LSIL (suspect CIN 1), and c) HSIL (CIN 2-3). The immunostained slides were analyzed by the densitometry software and scoring algorithm (Image-Pro® Plus; OPELCO; Dulles, Va.). The compatibility of the software and algorithm with the visual method for immunostaining analysis is shown in Table 2.

TABLE 2

Positive Cases Identified by HPV DNA and Protein Markers

| Clinical Specimen | Total # of Specimens | High Risk HPV DNA, # (%) Positive | PCNA + MIB-1 Proliferation Group, # (%) Positive | p16 Cell Cycle Control Group, # (%) Positive | PCNA +MIB-1 &/or p16, # (%) Positive | PCNA +MIB-1 &/or p16 & High Risk HPV DNA, # (%) Positive |
|---|---|---|---|---|---|---|
| WNL | 23 | 3 (13%) | 0 (0%) | 1 (4.3%) | 1 (4.3%) | 0 (0%) |
| LSIL (suspect CIN 1) | 21 | 19 (90.5%) | 11 (52.4%) | 2 (9.5%) | 11 (52.4%) | 9 (42.9%) |
| HSIL (suspect CIN 2-3) | 20 | 17 (85%) | 16 (80%) | 15 (75%) | 19 (95%) | 16 (80%) |

The results of Table 2 were interpreted in the same fashion as for Table 1. Briefly, 13% of the WNL specimens were found positive for high-risk HPV DNA, and 0% of the same specimens were positive for a combination of high-risk HPV DNA and either proliferation or cell cycle control markers. Additionally, 90.5% of the LSIL (suspect CIN 1) specimens were found positive for high-risk HPV DNA, and 42.9% of the same specimens were positive for a combination of high-risk HPV DNA and either proliferation or cell cycle control markers. Finally, 85% of the HSIL (suspect CIN 2-3) specimens were found positive for high-risk HPV DNA, and 80% of the same specimens were positive for a combination of high-risk HPV DNA and either proliferation or cell cycle control markers.

Alternatively, testing for protein markers may be performed using PCNA, MIB-1, and p16 as a single pool of antibodies with similar sensitivity as shown with two independent groups or double pools of antibodies. The same set of cervical specimens, analyzed using the software and scoring algorithm (Table 2), was used for antibody pool comparison. The following groups of specimens were tested: a) WNL, b) LSIL (suspect CIN 1), and c) HSIL (suspect CIN 2-3). The comparison data for double pools (PCNA+MIB-1 or p16) and a single pool (PCNA+MIB-1+ p16) of antibodies are presented in Table 3.

TABLE 3

Protein Expression Data for Single Marker Pool

| Clinical Specimens (same as in Table 2) | Total # of Specimens | Double Pools + High Risk HPV DNA, # (%) Positive | Single Pool + High Risk HPV DNA, # (%) Positive |
|---|---|---|---|
| WNL | 5 | 0 (0%) | 0 (0%) |
| LSIL (suspect CIN 1) | 21 | 9 (42.9%) | 8 (38.1%) |
| HSIL (suspect CIN 2-3) | 7 | 6 (85.7%) | 6 (85.7%) |

The high-risk HPV DNA and immunostaining results for double pools, either proliferation or cell cycle control group of markers, were previously identified (Table 2). A new set of data was generated by using a combination of high-risk HPV DNA and immunostaining results from the single pool of primary antibodies (PCNA, MIB-1, and p 16). Very similar results were scored for a combination of high-risk HPV DNA and either the single pool or double pools of antibodies. Briefly, the comparison data scored by either combination of antibodies pools with high-risk HPV DNA were identical for WNL (0% positive) and HSIL (suspect CIN 2-3) (85.7% positive) groups. Very marginal variation in percent positive cases between single pool plus HPV (38.1%) and double pools plus HPV (42.9%) was noted for LSIL (suspect CIN 1) group.

The immunostaining assay may also be performed using the preferred protein markers, PCNA and p16, individually. A new set of PC cervical specimens was used for this example. The specimens were grouped based on the received cytological diagnosis as followed: a) WNL, b) ASCUS, c) LSIL (suspect CIN 1), and d) HSIL (suspect CIN 2-3). All groups were tested for high-risk HPV DNA by the HC2 test. PCNA and p16 protein expression was performed by the immunostaining assay. The results scored by the software algorithm (Image-Pro® Plus (OPELCO; Dulles, Va.)) are presented in Table 4.

TABLE 4

Positive Cases Identified by HPV DNA and Preferred Protein Markers

| Clinical specimens | Total # of specimens | High risk HPV DNA, # (%) positive | PCNA proliferation group, # (%) positive | P16 cell cycle control group, # (%) positive | PCNA &/or p16, # (%) positive | PCNA &/or p16 & High Risk HPV DNA, # (%) positive |
|---|---|---|---|---|---|---|
| WNL | 102 | 8 (8%) | 26 (26%) | 11 (11%) | 27 (27%) | 3 (3%) |
| ASCUS | 88 | 42 (48%) | 39 (44%) | 22 (25%) | 46 (52%) | 25 (28%) |
| LSIL (suspect CIN 1) | 92 | 79 (86%) | 47 (51%) | 15 (16%) | 49 (53%) | 44 (48%) |
| HSIL (suspect CIN 2-3) | 85 | 81 (95%) | 69 (81%) | 56 (66%) | 75 (88%) | 71 (84%) |

A total of 102 WNL cervical specimens were tested for high-risk HPV DNA. The presence of high-risk HPV DNA was found in 8 out of 102 (8%) WNL specimens. The same group of specimens was tested for expression of preferred protein markers (PCNA and p 16) by the immunostaining protocol. Positive PCNA expression was found in 26 out of 102 (26%) WNL specimens. Positive p16 expression was found in 11 out of 102 (11%) WNL specimens. Overall, we found 27 out of 102 (27%) WNL specimens positive for PCNA or p16 expression. The combination of high-risk HPV DNA and preferred protein markers tests demonstrated 3 out of 102 (3%) positive for the WNL group. The rest of the results were interpreted in a similar fashion. Briefly, 48% of ASCUS specimens were found positive for high-risk HPV DNA, and 28% of the same specimens were positive for a combination of high-risk HPV DNA and either proliferation or cell cycle control markers. Additionally, 86% of the LSIL (suspect CIN 1) specimens were found positive for high-risk HPV DNA, and 48% of the same specimens were positive for a combination of high-risk HPV DNA and either marker. Finally, 95% of the HSIL (suspect CIN 2-3) specimens were found positive for high-risk HPV DNA, and 84% of the same specimens were positive for a combination of high-risk HPV DNA and either marker.

For example, Table 4 illustrates the increasing specificity and reduction of clinical false positive results as the HPV nucleic acid test is combined with the molecular marker test. Of the WNL specimens, 8% are positive as determined by the HPV nucleic acid test alone, while protein marker tests of the WNL specimens result in 11%-27% positive results. However, the combination of the high risk HPV DNA primary screen and the protein marker secondary screen results in only 3% of the WNL specimens as positive. This significant reduction in positive results is due to the reduction of clinical false positive results or in other words, specimens that are HPV DNA positive but are from women who do not appear to have clinical disease. The HPV DNA test results are not suggested to be analytically false positive, but in the vast majority of cases, the HPV DNA is actually present in such HPV DNA test positive cases in clinically non-diseased women. Accordingly, this sequential or concurrently sequential method is accurate, sensitive, and reduces the number of false positives by the range of about 15%-100%, about 20%-90%, or about 30%-70%.

Additional markers, such as mcm2, mcm5, and p14ARF, can be utilized in combination with either high-risk HPV DNA and PCNA or high-risk HPV DNA and any marker (PCNA, p16, mcm2, mcm5, p14ARF). The same set of cervical specimens, as shown in Table 3, was used for evaluation of the additional markers. mcm2 expression was measured using monoclonal mouse anti-human mcm2 antibody (code #ab6153, Abcam Limited, Cambridge, UK). mcm5 expression was measured using monoclonal mouse anti-human mcm5 antibody (code #ab6154, Abcam Limited, Cambridge, UK). Finally, p14ARF expression was measured using monoclonal mouse anti-human p14ARF antibody (14PO3, code #MS-1115-P, Lab Vision Corporation, Fremont, Calif., USA). The clinical evaluation of mcm2, mcm5, and p14ARF is shown in Table 5.

TABLE 5

Positive Cases Identified by HPV DNA, PCNA, p16, mcm2, mcm5, and p14

| Clinical Specimens | Total # of Specimens | High Risk HPV DNA, # (%) Positive | Mcm2 &/or PCNA & High Risk HPV DNA, # (%) Positive | Mcm5 &/or PCNA & High Risk HPV DNA, # (%) Positive | P14 &/or PCNA & High Risk HPV DNA, # (%) Positive | Any Marker* & High Risk HPV DNA, # (%) Positive |
|---|---|---|---|---|---|---|
| WNL | 38 | 6 (16%) | 3 (8%) | 4 (11%) | 3 (8%) | 4 (11%) |
| ASCUS | 40 | 22 (55%) | 14 (35%) | 15 (38%) | 15 (38%) | 15 (38%) |
| LSIL (suspect CIN 1) | 37 | 31 (84%) | 21 (57%) | 24 (65%) | 22 (59%) | 24 (65%) |
| HSIL (suspect CIN 2-3) | 40 | 38 (95%) | 32 (80%) | 33 (83%) | 34 (85%) | 36 (90%) |

*PCNA, p16, mcm2, mcm5, p14

A total of 38 WNL cervical specimens were tested for high-risk HPV DNA. The presence of high-risk HPV DNA was found in 6 out of 38 (16%) WNL specimens. The same group of specimens was tested for expression of preferred protein markers (PCNA and p16) and additional protein markers (mcm2, mcm5, and p14) by the immunostaining protocol. The combination of high-risk HPV DNA and either PCNA and/or mcm2 tests demonstrated 3 out of 38 (8%) positive for WNL specimens. The combination of high-risk HPV DNA and either PCNA and/or mcm5 tests demonstrated 4 out of 38 (11%) positive for the same specimens. The combination of high-risk HPV DNA and either PCNA and/or p14 tests demonstrated 3 out of 38 (8%) positive for this group. Finally, we found 4 out of 38 (11%) WNL specimens positive for high-risk HPV DNA and combination of any protein markers, PCNA, p16, mcm2, mcm5, and p14. The rest of the results were interpreted in a similar fashion.

Future molecular staging and classification for potentially progressive cervical disease may be performed as demonstrated in Tables 7 and 8. The hypothesis is related to grouping the specimens based on their similarities in being positive for the spectrum of molecular events or hits. For example, the cases negative for high-risk HPV DNA could be staged as MG0. This grade signifies the absence of high-risk HPV infection and neoplastic lesions. The cases positive for high-risk HPV DNA and negative for either protein marker could be staged as Molecular Grade I (MG). This grade possibly could signify a small low grade lesion with low exfoliation of abnormal cells or latent high-risk HPV infection (since no additional molecular marker positives are detectable), which either could lead to spontaneous viral clearance or persistence. The cases positive for both high-risk HPV DNA and either group of markers could be staged as MG II. (Using a panel of markers would possibly allow for identification of sub-grades based on variation of positive markers per case.) This grade represents specimens with cervical neoplastic lesions, either low- and/or high-grade lesions, since the highest molecular activity score is measured. It is the dramatically increased risk of high-grade neoplastic HSIL (suspect CIN 3+) disease in MGII that is of greatest importance and interest for users of the disease grade assessment strategy described herein.

Table 6 utilized the group of specimens, WNL, ASCUS, LSIL (suspect CIN 1), HSIL (suspect CIN 2-3), from Table 5 and the HSIL (suspect CIN 3+) specimens were the same as those used in Table 2. MG0, or neoplastic disease free women, were found to comprise 84%-97% of the WNL group. The same (WNL) group was staged within 3%-8% for MG I and 0%-8% for MG II. MG0 was staged for 45%-58% of women with ASCUS diagnosis. The ASCUS group was staged within 19%-20% and 23%-35% for MG I and MG II, respectively. MG0 was staged for 13%-16% of women with LSIL (suspect CIN 1) diagnosis. The LSIL (suspect CIN 1) group was shown to have about equal representation of MG I and MG II (30%-40% and 44%-54%, respectively). In contrast, the majority of HSIL (suspect CIN 2-3 and HSIL (suspect CIN 3+) groups were classified as MG II (82%-84% and 100%, respectively). MG0 was staged in 4%-5% and 0% of women with HSIL (suspect CIN 2-3) and HSIL (suspect CIN3+) diagnoses, respectively. The molecular screening tests for cervical cancer may allow for categorization of the specimens in relation to neoplastic grade, as shown above. Thus, molecular grades may be used for more accurate medical follow-up procedures.

A 95% confidence interval gives an estimated range of values which are likely to include with 95% confidence, the estimated true but unknown population mean parameter, the estimated range being calculated from a given set of sample data. The 95% and 99% confidence intervals which have 0.95 and 0.99 probabilities of containing the parameter respectively are most commonly used. If independent sets of samples are taken repeatedly from the same population, and a confidence interval calculated for each set of samples, then 95% of such estimated intervals (confidence level) will contain the true but unknown population parameter. The confidence interval represents the range of values, consistent with the data, that is believed to encompass the "true" value with 95% probability. The confidence interval is expressed in the same units as the estimate. Wider intervals indicate lower precision; narrow intervals, greater precision.

TABLE 6

Potential Molecular Staging (MG) of Cervical Neoplasia

| Clinical Specimens | Total # of Specimens | MG0, # (%) Positive | MG I, # (%) Positive | MG II, # (%) Positive |
|---|---|---|---|---|
| WNL | 102 | 84%-97% | 3%-8% | 0%-8% |
| ASCUS | 88 | 45%-58% | 19%-20% | 23%-35% |
| LSIL (suspect CIN 1) | 92 | 13%-16% | 30%-44% | 44%-54% |
| HSIL (suspect CIN 2-3) | 85 | 4%-5% | 11%-13% | 82%-84% |
| HSIL (suspect CIN 3+) | 19 | 0% | 0% | 100% |

TABLE 7

Potential Molecular Staging (MG) Of Cervical Neoplasia With 95% Confidence Intervals (CI)

| Clinical Specimens | Total # of Specimens | MG 0, # of Specimens | MG 0, 95% CI | MG I, # of Specimens | MG I, 95% CI | MG II, # of Specimens | MG II, 95% CI |
|---|---|---|---|---|---|---|---|
| WNL | 102 | 94 | 0.9216 (0.8513, 0.9655) | 5 | 0.0490 (0.0161, 0.1107) | 3 | 0.0294 (0.0061, 0.0836) |
| ASCUS | 88 | 46 | 0.5227 (0.4135, 0.6304) | 17 | 0.1932 (0.1168, 0.2912) | 25 | 0.2841 (0.1930, 0.3902) |
| LSIL (suspect CIN 1) | 92 | 13 | 0.1413 (0.0774, 0.2295) | 35 | 0.3804 (0.2812, 0.4876) | 44 | 0.4783 (0.3730, 0.5850) |
| HSIL (suspect CIN 2-3) | 85 | 4 | 0.0471 (0.0130, 0.1161) | 10 | 0.1176 (0.0579, 0.2057) | 71 | 0.8353 (0.7391, 0.9069) |
| HSIL (suspect CIN 3+) | 19 | 0 | 0.0000 (0.0000, 0.1765) | 0 | 0.0000 (0.0000, 0.1765) | 19 | 1.0000 (0.8235, 1.0000) |

The 95% confidence interval analysis of the data of Table 7 suggested that 92.16% of the WNL specimens were MG0 in the WNL population, where the WNL population characterized as MG0 falls within 85.13% to 96.55%; 4.9% of the WNL specimens were MGI in the WNL population, where the WNL population characterized as MGI falls within 1.6% to 11.07%; 2.94% of the WNL specimens were MGII in the WNL population, where the WNL population characterized as MGII falls within 0.61% to 8.36%; 52.27% of the ASCUS specimens were MG0 in the ASCUS population, where the ASCUS population characterized as MG0 falls within 41.35% to 63.04%; 19.32% of the ASCUS specimens were MGI in the WNL population, where the ASCUS population characterized as MGI falls within 11.68% to 29.12%; 28.41% of the ASCUS specimens were MGII in the ASCUS population, where the ASCUS population characterized as MGII falls within 19.30% to 39.02%; 14.13% of the LSIL (suspect CIN 1) specimens were MG0 in the LSIL (suspect CIN 1) population, where the LSIL (suspect CIN 1) population characterized as MG0 falls within 7.74% to 22.95%; 38.04% of the LSIL (suspect CIN 1) specimens were MGI in the LSIL (suspect CIN 1) population, where the LSIL (suspect CIN 1) population characterized as MGI falls within 28.12% to 48.76%; 47.83% of the LSIL (suspect CIN 1) specimens were MGII in the LSIL (suspect CIN 1) population, where the LSIL (suspect CIN 1) population characterized as MGII falls within 37.30% to 58.50%; 4.71% of the HSIL (suspect CIN 2-3) specimens were MG0 in the HSIL (suspect CIN 2-3) population, where the HSIL (suspect CIN 2-3) population characterized as MG0 falls within 1.3% to 11.61%; 11.76% of the HSIL (suspect CIN 2-3) specimens were MGI in the HSIL (suspect CIN 2-3) population, where the HSIL (suspect CIN 2-3) population characterized as MGI falls within 5.79% to 20.57%; 83.53% of the HSIL (suspect CIN 2-3) specimens were MGII in the HSIL (suspect CIN 2-3) population, where the HSIL (suspect CIN 2-3) population characterized as MGII falls within 73.91% to 90.69%; 0.0% of the HSIL (suspect CIN 3+) specimens were MG0 in the HSIL (suspect CIN 3+) population, where the HSIL (suspect CIN 3+) population characterized as MG0 falls within 0% to 17.65%; 0% of the HSIL (suspect CIN 3+) specimens were MGI in the HSIL (suspect CIN 3+) population, where the HSIL (suspect CIN 3+) population characterized as MGI falls within 0% to 17.65%; and 100% of the HSIL (suspect CIN 3+) specimens were MGII in the HSIL (suspect CIN 3+) population, where the HSIL (suspect CIN 3+) population characterized as MGII falls within 82.35% to 100%.

CONCLUSION

By comparing testing results for high risk HPV DNA coupled with cytology with results obtained for high risk HPV DNA and markers, the incidence of positive cases was reduced from 8% to 3% for WNL, from 48% to 28% for ASCUS, and from 86% to 48% for LSIL (suspect CIN 1) (Table 4). A few WNL specimens were positive for high-risk HPV DNA (6.5% from Table 1 and 8% from Table 4). These specimens, although without detectable cytological abnormalities, may be at higher risk of developing neoplastic lesions. However, 0% to 3% of these HPV positive WNL specimens were positive for either PCNA and/or p16 protein markers. Thus, a very low rate of HPV DNA in combination with markers that are positive was demonstrated in cytologically normal women. In contrast, a relatively high percent of WNL specimens were positive for either protein markers (30.4% in Table 1 and 27% in Table 4), suggesting the limited specificity of the protein markers as an individual test. However, the combination of tests for high-risk HPV DNA and protein markers demonstrated very high sensitivity (Table 1) for HSIL (suspect CIN 3+) group, which comprises lesions much less likely to show spontaneous regression to normal cytology and an increased risk of progression to cancer. Relatively high sensitivity of the same test combination was demonstrated for the HSIL (suspect CIN 2-3) group (84% in Table 4).

The data from Table 4 indicate that the addition of a molecular marker test to HPV DNA may significantly improve specificity of HPV DNA for potential high grade lesions and cancer. The presence of high-risk HPV DNA was demonstrated in 48% and 86% of ASCUS and CIN 1 specimens, respectively. Additional test for protein markers reduces HPV positives by 20% and 38% for ASCUS and LSIL (suspect CIN 1) groups, respectively. High-risk HPV DNA test helped to reduce the cases that are less likely to have or progress to high grade lesion or cancer in ASCUS and LSIL (suspect CIN 1) groups by 52% (considering 88 ASCUS women as 100%) and by 14% (considering 92 LSIL women as 100%), respectively. Additional tests for protein markers reduced HPV positives with concurrent marker staining by 20% and 38% for ASCUS and LSIL (suspect CIN1) groups, respectively. Furthermore, the combination of high risk HPV DNA with molecular markers tests helped to reduce the cases that are less likely to have or progress to high grade lesion or cancer in ASCUS and LSIL (suspect CIN 1) groups by 72% and 52%, respectively. Overall, reduction of test positivity in women who are less likely to have high-grade lesion or cancer is beneficial and can be achieved by implementing the combination of high-risk HPV DNA with protein markers for the ASCUS and LSIL (suspect CIN1) groups, respectively. Therefore, the data demonstrate the ability of categorizing high-risk HPV DNA positive specimens into lesions that are more likely to be high grade as opposed to low grade by adding protein markers testing to HPV DNA screening. These data also indicate the potential clinical significance of the novel molecular diagnostic method for possibly more accurate and specific diagnosis of ASCUS and LSIL (suspect CIN 1) lesions. The potential improved specificity of high-risk HPV DNA through molecular marker testing enables novel cervical cancer screening to be a useful tool for women of all ages.

Furthermore, the hypothesis and preliminary data supporting the possibility of molecular classification of potentially progressive cervical disease were described. These results indicate the possibility of classifying exfoliated cervical cell specimens according to the molecular stage of the underlying SIL lesions when using the combination of high risk HPV DNA and the markers (Tables 7 and 8) in the absence of information on the cytology grading and thus this strategy constitutes a novel molecular HPV-markers test superior to Pap and HPV-Pap tests. The information on high-risk HPV DNA types may help to detail molecular grades into sub-grades. Overall, the data support the utility of the novel molecular method for cervical cancer diagnosis.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

REFERENCES

1. Ponten et al. *Int J Cancer* 60:1-26, 1995.
2. Russell L. *Educated Guesses: Making Policy About Medical Screening Tests*. Berkeley, University of California Press, 6-24, 1994.
3. American Cancer Society, *Cancer Facts and Figures,* 2000, Atlanta, Ga.
4. Sherman et al. *Cancer* 84: 273-80, 1998.
5. Brown et al. *JAMA* 281:347-53, 1999.
6. Schechter, *Acta Cytol.* 40: 1272-82, 1996.
7. Sawaya et al. *Obstet Gynecol* 94:307-10, 1999.
8. Mandelblatt et al. *JAMA* 287:2372-81, 2002.
9. Sherman et al. *J Natl Cancer Inst* 94:102-7, 2002.
10. Vassilakos et al. *Br J Cancer* 86:382-8, 2002.
11. Weaver et al. *Acta Cytol* 44:301-4, 2000.
12. Lin, et al. *Am J Obstet Gynecol* 183:39-45, 2000.
13. Patterson et al. *Acta Cytol* 45:36-47, 2001.
14. Walboomers et al. *J Pathol* 189:12-9, 1999.
15. Doeberitz, *Pap Report* 13: 65-74, 2002.
16. Feichter et al., *Acta Cytol* 46:630-2, 2002.
17. Jeon et al., *J. Virol.* 69(5):2989-2997, 1995.
18. Bosch et al., *J Clin Pathol* 55:244-65, 2002.
19. Brooks et al., *Br J Cancer* 86:263-8, 2002.
20. Keesee et al. *Anal Quant Cytol Histol* 24:137-46, 2002.
21. Bibbo et al. *Acta Cytol* 46: 25-9, 2002.
22. Tjalma et al., *European J of Obstet & Gyn and Reproductive Biology* 97: 223-230, 2001.
23. Keating et al., *The American J of Surgical Pathology* 25: 884-91, 2001.
24. Keating et al., *Advances in Anatomic Pathology,* 8: 83-92, 2001.
25. Sano et al., *Pathology International* 52: 375-83, 2002.

What is claimed is:

1. A kit for detecting high risk HPV nucleic acids and subsequently detecting protein marker expression in a sample, comprising reagents for detecting molecular characteristics in a biological sample, wherein the reagents consist essentially of at least two probes capable of detecting high risk HPV nucleic acids in a sample, at least two primary antibodies that are specific to two different protein markers, wherein the protein markers are selected from the group consisting of: PCNA and Ki-67, PCNA and p16, and PCNA, Ki-67 and p16.

2. The kit according to claim 1, wherein the at least two probes are selected from the group consisting of a DNA probe and an RNA probe.

3. The kit of claim 1, wherein the kit further comprises instructions for detecting the HPV nucleic acids by hybridization under low stringency conditions.

4. The kit of claim 1, wherein the protein markers are PCNA and Ki-67.

5. The kit of claim 1, wherein the protein markers are PCNA and p16.

6. The kit of claim 1, wherein the protein markers are PCNA, Ki-67 and p16.

* * * * *